United States Patent [19]

Bailly

[11] Patent Number: 4,539,982
[45] Date of Patent: Sep. 10, 1985

[54] ODOR ABSORBING WRAP

[76] Inventor: Richard L. Bailly, Beechwood Cir., Boxford, Mass. 01921

[21] Appl. No.: 643,775

[22] Filed: Aug. 24, 1984

Related U.S. Application Data

[63] Continuation-in-part of Ser. No. 544,500, Oct. 24, 1983, Pat. No. 4,469,740, which is a continuation-in-part of Ser. No. 470,606, Feb. 28, 1983, Pat. No. 4,461,099.

[51] Int. Cl.³ ............... A61L 15/00; B32B 3/12; B32B 7/02; B32B 7/04
[52] U.S. Cl. ................. 128/156; 428/283; 428/300; 428/304.4; 428/317.9
[58] Field of Search ........... 428/304.4, 316.6, 317.9, 428/283, 300; 128/156

[56] References Cited

U.S. PATENT DOCUMENTS

| | | | |
|---|---|---|---|
| 3,852,897 | 12/1974 | Bridge | 36/44 |
| 4,045,609 | 8/1977 | Hart | 428/317.9 |
| 4,062,131 | 12/1977 | Hsiung | 36/44 |
| 4,099,342 | 7/1978 | Singh | 428/304.4 |
| 4,137,110 | 1/1979 | Singh | 428/308.4 |
| 4,185,402 | 1/1980 | Digate | 36/44 |
| 4,192,086 | 3/1980 | Sichak | 36/44 |
| 4,433,024 | 2/1984 | Eian | 428/283 |
| 4,461,099 | 7/1984 | Bailly | 428/317.9 |
| 4,469,740 | 9/1984 | Bailly | 428/316.6 |

*Primary Examiner*—William J. Van Balen
*Attorney, Agent, or Firm*—Lahive & Cockfield

[57] ABSTRACT

Disclosed is a flexible, odor-absorbing web for use under casts or other devices used in prolonged close contact with the human body. The web comprises a sheet-like matrix comprising an open-celled or closed-celled foam, or cellulosic fibers in a binder, filled with activated carbon particles. On the surface of the matrix designed for contact with the skin is a hydrophobic fiber layer, preferably needle-punched into the carbon-containing matrix. The opposite surface of the matrix may include a hydrophilic fiber layer.

13 Claims, 6 Drawing Figures

ODOR ABSORBING WRAP

REFERENCE TO RELATED APPLICATION

This application is a continuation-in-part of copending application Ser. No. 544,500, now U.S. Pat. No. 4,469,740 filed Oct. 24, 1983, which is a continuation-in-part of U.S. application Ser. No. 470,606, now U.S. Pat. No. 4,461,099, filed Feb. 28, 1983.

BACKGROUND

This invention relates to an odor-absorbing wrap for use in close contact with the human body, for example, under a cast or splint. More particularly, the invention relates to a flexible, odor-absorbing composite material which wicks away and dissipates perspiration and absorbs odor-causing components emanating from the surface of the skin.

Individuals who must wear a splint or cast of plaster or other materials for a significant amount of time during healing of a fracture or in connection with other orthopedic corrective procedures perspire beneath the cast. Typically, a wrap of cotton or the like is applied beneath the cast for cushioning purposes. Over time, the cloth wrap absorbs perspiration and the odor-causing substances it contains, and the patient detects offensive odors. A similar problem may arise in connection with wraps used by athletes during exercise.

Webs of material containing activated charcoal can make an effective odor-absorbing material. An example is odorabsorbing innersoles which comprise a matrix containing activated carbon particles. To be effective, such materials must be permeable to vapors and liquids, and a large surface area of the activated carbon must be available for adsorption.

The greatest effort in designing odor-absorbing materials has apparently been concentrated in innersole technology as disclosed, for example, in U.S. Pat. Nos. 3,852,897, 4,062,131, 4,099,342, 4,137,110, 4,185,402, and 4,192,086. Odor-absorbing structures also have been devised for use in various clinical procedures. For example, U.S. Pat. No. 3,868,955 discloses a dressing for absorbing body fluid which reduces unpleasant odors because it includes an aldehyde polysaccharide. U.S. Pat. No. 4,128,686 discloses a sheetlike assembly for the management of incontinence comprising hydrophobic and hydrophilic layers which may include an antimicrobiol agent to reduce urine odor.

None of the foregoing patents deal with the peculiar problem of providing a flexible, comfortable, odor-absorbing material for use under casts and the like or for support during exercise.

Accordingly, it is an object of the invention to provide a flexible composite material that wicks perspiration away from the body, absorbs odors, and is comfortable when maintained in direct contact with the skin.

These and other object and features of the invention will be apparent from the following description, from the drawing, and from the claims.

SUMMARY OF THE INVENTION

In one aspect, the invention comprises an odor-absorbing web for use in wrapping a portion of the body. The web comprises a thin, flexible sheet which serves as a matrix for binding together a multiplicity of activated charcoal, odor-absorbing particles. A hydrophobic fibrous material is affixed to a first surface of the sheet for placement in contact with the body surface. Preferably a hydrophilic fibrous material is fixed to the opposite surface.

In preferred embodiments, the matrix comprises cellulosic fibers in a latex binder or a flexible elastomeric open-celled foam, e.g., polyurethane, containing dispersed activated charcoal particles. The hydrophobic fibrous material may comprise a woven or non-woven hydrophobic fibrous material adhered to the surface of the matrix but most preferably comprises a non-woven layer of close packed hydrophobic fibers, a substantial fraction of which penetrates the matrix. Such structures can be fabricated by needle-punching short fibers placed on the surface of the matrix to form a substantially continuous, soft, hydrophobic layer. The optional hydrophilic fibrous material on the surface opposite the hydrophobic fibers may likewise be adhered to the matrix, but preferably comprises a non-woven, needle-punched, close-packed layer of hydrophilic fibers.

In the preferred embodiments of the invention the hydrophobic fibers in contact with the body wick perspiration and the odor-causing substances it contains away from the skin and into the odor-absorbing matrix where the odor-causing materials are adsorbed on the activated charcoal. The presence of the hydrophilic layer on the surface of the matrix opposite the skin serves to provide additional cushioning between the cast or splint and the skin's surface. It also aides in evaporation of perspiration.

In another aspect, the invention comprises a process for reducing odors beneath a cast, splint, or other device designed for contact with the human body comprising the step of applying, preferably as a winding, the odor absorbent composite material of the invention to the area to be covered prior to installation of the device, with the hydrophobic layer in contact with the skin.

BRIEF DESCRIPTION OF THE DRAWING

Like reference characters in the respective drawn Figures indicate corresponding components.

DESCRIPTION

Figure 1A:
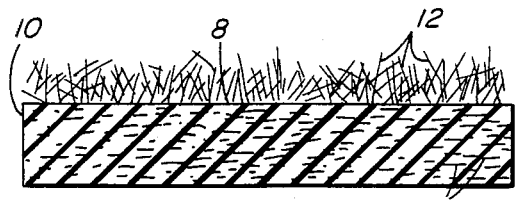
FIG. 1 illustrates a composite material comprising a first exemplary embodiment of the invention shown during various stages of its manufacture.

Referring to the drawing, an exemplary embodiment of the invention is illustrated in FIG. 1 at several stages of its manufacture. In the first stage, a flexible, foam plastic sheet 10 containing a multiplicity of activated carbon particles 6 uniformly dispersed therein is covered at surface 8 with a layer of short hydrophobic fibers 12.

Foams containing dispersed activated carbon particles suitable for use in this embodiment of the invention are available commerically from, for example, Lewcott Chemical Company, Scott Foam Company, and Advanced Absorber Company. The layer 10 can comprise an elastomeric, open-celled foam, preferably polyurethane, made by processes known to those skilled in the art. Other foams and other flexible, activated carbon-filled sheet materials also may be used. All such foamed polymeric matrices are preferably open-celled so that transport of perspiration and the like is facilitated and the exposed surface area of the activated carbon particles is optimized. However, the needling process conducted during the course of manufacture of certain embodiments of the invention as disclosed below greatly facilitates moisture transport. Accordingly closed cell foams may be used.

The hydrophobic fibers may comprise polypropylene, polyester, or other known materials. The length of the fibers depends on the overall thickness of the odor-absorbing wrap being manufactured. The fibers are preferably thin, e.g., 12-22 microns in diameter, but smaller diameter fibers may be used and tend to provide an even softer surface. Also, while in the illustration the fibers 12 are depicted as being randomly oriented, the fibers are preferably passed through a carding machine which orients them in parallel or cross-layed fashion to form a more uniform non-woven product.

The fibers are used at a density on the order of 2-10 ounces per square yard of matrix, preferably about 6 ounces per square yard. Such hydrophobic fibers are known to have the ability to wick perspiration away from the body along the axis of the fiber.

Figure 1B:
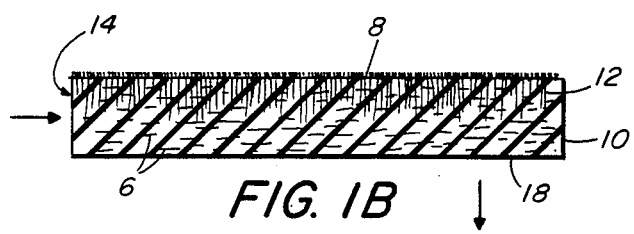

The non-woven fibers 12 and the matrix 10 are made integral during a needling process wherein the fibers are threaded into the layer 10 and locked together to form a soft top layer 14 comprising a substantially continuous non-woven layer of close-packed fibers (see FIG. 1b). By punching holes and imbedding water-transporting fibers downwardly through the odor-absorbing layer 10, the needling process makes the odor-absorbing layer 10 and the activated particles 6 it contains readily accessible to moisture and odor-causing substances from the skin. Accordingly, in the preferred needled form of the invention there is no need separately to form openings for the purposes of exposing activated carbon particle.

Flexible foam plastic carbon-filled matrices of the type described above are typically somewhat elastomeric and may be slightly stretched on application as a winding or the like to the body surface. As disclosed hereinafter, a woven hydrophobic mat may be used in place of the needled layer. However, in embodiments comprising elastomeric matrices, non-woven fibers are preferred as they tend to interfere less with the elasticity of the matrix 10.

Figure 1D:
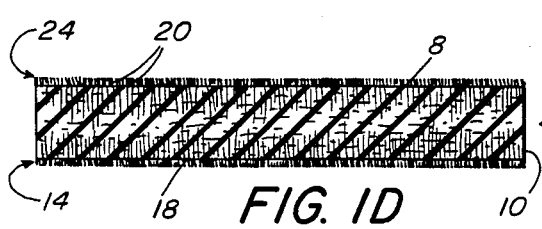
Figure 1C:
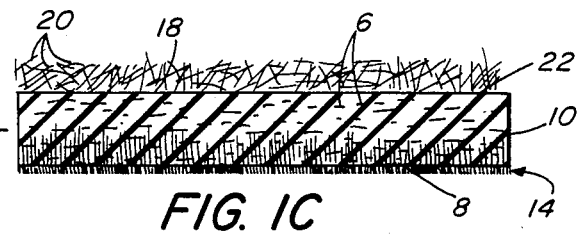

The composite material depicted in FIG. 1b may be used as is, with layer 14 in contact with the surface of the body, but preferably is further treated as depicted in FIGS. 1c and 1d to incorporate a needled hydrophilic layer on the surface 18 of matrix 10. Thus, the hydrophilic fibers, e.g., rayon or cotton fibers 20, are randomly placed or oriented as desired on the surface 18 opposite surface 8 of matrix 10 and needle-punched as described above to produce a hydrophilic, non-woven, substantially continuous layer depicted at 24. The presence of the hydrophilic layer serves to provide increased cushioning beneath the cast or splint with which the composite material of the invention is to be used and can promote evaporation of perspiration. Thus, in use, perspiration generated at the skin surface is wicked by layer 14 of hydrophobic fibers 12 into the matrix 10 where activated charcoal particles 6 adsorb its odor-causing components. The aqueous components of the perspiration are absorbed by hydrophilic fibers 20 and transported through the matrix 10 to the space, if any, between the cast and the wrap.

Figure 2:
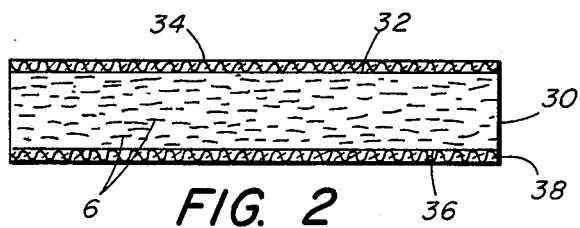
FIG. 2 is an illustration of a composite material comprising a second exemplary embodiment of the invention.

Referring to FIG. 2, a second embodiment of the invention is shown. It comprises an odor-absorbing, activated carbon-filled matrix 30 of cellulosic fibers and a binder. The odor-absorbing matrix 30 must be flexible enough to conform to the skin surface to be wrapped. A preferred layer 30 for use in the invention is available commercially from Purification Products, Ltd., West Yorkshire, England, and is sold under the trade names "Odasorb" or "Garfil". This material, sold in sheet form, comprises activated carbon particles and wood pulp fibers in a latex binder. Details of the materials and construction of such odor-absorbing sheets are disclosed in U.S. Pat. Nos. 4,317,110, 4,099,342, and 3,852,897, the disclosures of which are incorporated herein by reference. The content of activated carbon in layer 30 is preferably at least 20 percent, and the more carbon the better provided that the layer's tear strength does not deteriorate to the point where the web is damaged during application.

Affixed to a first surface 32 of web 30 is a loosely woven hydrophobic fibrous material 34. Similarly, surface 36 of web 30 is covered with a hydrophilic woven fibrous material 38. Non-woven webs of hydrophobic fibrous material (not shown) may be substituted for the woven web.

The material may conveniently be adhered integrally with the cellulosic web 30 by means of conventional bonding techniques. Flame laminating or perforated film adhesion may be used. Flame laminating involves a thin layer of, e.g., open-celled urethane, which is passed over an open flame. The resulting tacky film is then laminated between the fibrous layer 34 and matrix 30 as it is passed through the nip of a cooled roller. The combination of heat loss and pressure results in an open-celled bond which permits transmission of liquids and vapors. Perforated film adhesion involves the use of a thermoplastic perforated film as a bonding agent. A thin sheet of, e.g., perforated polyethylene, is sandwiched between the fibrous layer 34 and matrix 30, and is then passed through the nip of a heated roller maintained at a temperature sufficient to soften the film as heat flows through the fibrous layer without adversely affecting the fibrous layer. Again, a porous bond is formed which permits transport of liquids and vapors, permitting the hydrophobic fibers to wick perspiration away from the skin and into contact with the charcoal-filled matrix. Porous films suitable for use in this process are available commercially from, for example, Ethyl Corporation and Xiro, Ltd. of Switzerland.

Similar techniques may be used to adhere the hydrophilic fibrous material.

It is also possible to employ the needle-punching process to attach a woven or non-woven hydrophilic or hydrophobic layer to the matrix. Another possible variation is to bond a porous web of hydrophobic or hydrophilic fibers to a previously formed needle-punched layer by means of one of the bonding processes set forth above or other processes.

It should be understood from the foregoing that one or both surfaces of cellulosic matrix 30 may be needle-punched as described with reference to FIG. 1, and further that one or both surfaces of matrix 10 may be covered with an adhered woven or non-woven fibrous material as described with reference to FIG. 2. In general, best odor-absorbing results are achieved if the hydophobic layer is formed by needle-punching. The needled fibers also significantly reinforce the cellulosic web 30, thereby making it more resistant to tearing. As noted above, the hydophilic layer may be eliminated entirely if the reduction in evaporation rate of perspiration can be tolerated.

Figure 3:
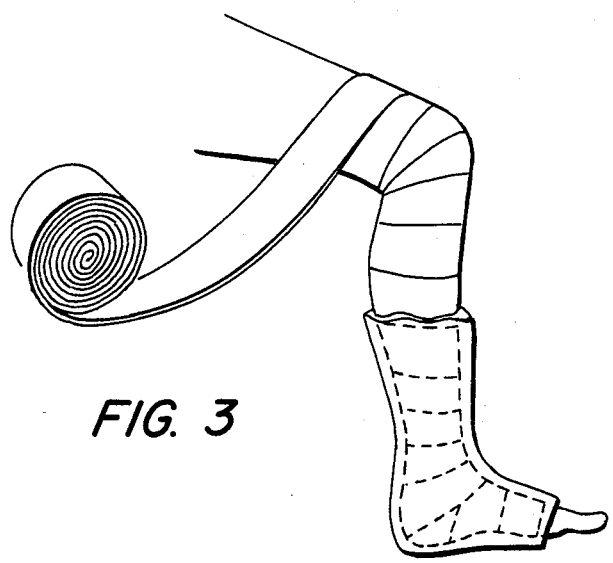
FIG. 3 is a schematic drawing illustrating the use of the odor-absorbing composite material of the invention.

While the flexible, odor-absorbing composite material of the invention may be fabricated in any sheet form, it is preferably manufactured as a roll of material, e.g., 3 to 6 inches wide. As shown in FIG. 3, a roll of such material may be wrapped about an area of the body before applying a cast, brace, or other orthopedic or prosthetic device, or for support during athletic activity, and secured by clips, tape, or other conventional means. The application of multiple layers of plaster-soaked cloth strips to form a conventional plaster cast may create a bond between the cast and the hydrophilic layer, if used. This produces a soft, inner, odor-absorbing layer integral with the cast itself.

The invention may be embodied in other specific forms without departing from the spirit and scope thereof. Accordingly, other embodiments are within the following claims.

What is claimed is:

1. An odor-absorbing web for use in wrapping a portion of the body, said web comprising:
   a thin, flexible sheet comprising a matrix binding together a multiplicity of activated charcoal odor-absorbing particles; and
   a hydrophobic material comprising a multiplicity of hydrophobic fibers, a substantial fraction of which penetrates said matrix, affixed to a first surface of said sheet for placement in contact with a body surface.

2. The web of claim 1 further comprising a hydrophilic fibrous material affixed to a surface opposite said first surface of said sheet.

3. The web of claim 1 wherein said matrix comprises cellulosic fibers in a latex binder.

4. The web of claim 1 wherein said matrix comprises an elastomeric foam.

5. The web of claim 4 wherein said foam is an open-celled foam.

6. The web of claim 4 wherein said foam is a polyurethane foam.

7. The web of claim 3 wherein said hydrophobic fibrous material is adhered to said sheet.

8. The web of claim 4 wherein said hydrophobic fibrous material is adhered to said sheet.

9. The web of claim 3 wherein said hydrophobic fibrous material comprises a non-woven layer of close-packed hydrophobic fibers.

10. The web of claim 4 wherein said hydrophobic fibrous material comprises a non-woven layer of close-packed hydrophobic fibers.

11. The web of claim 2 wherein said hydrophilic fibrous material comprises a non-woven layer of close packed hydrophilic fibers, a substantial fraction of which penetrate said matrix.

12. The web of claim 2 wherein said hydrophilic fibrous material is adhered to said sheet.

13. A process for reducing odor beneath a device used in close proximity to the surface of the human body, said process comprising the step of applying to said body surface the web of claim 1 with said first surface facing toward said body surface prior to application of said device.

* * * * *